United States Patent
Moctezuma de la Barrera et al.

(10) Patent No.: US 8,082,022 B2
(45) Date of Patent: *Dec. 20, 2011

(54) SYSTEM, DEVICE, AND METHOD FOR DETERMINING A POSITION OF AN OBJECT

(75) Inventors: Jose Luis Moctezuma de la Barrera, Freiburg (DE); Chunwu Wu, Kalamazoo, MI (US)

(73) Assignee: Stryker Leibinger GmbH & Co., KG, Freiburg (DE)

( * ) Notice: Subject to any disclaimer, the term of this patent is extended or adjusted under 35 U.S.C. 154(b) by 125 days.

This patent is subject to a terminal disclaimer.

(21) Appl. No.: 12/644,298

(22) Filed: Dec. 22, 2009

(65) Prior Publication Data

US 2010/0099983 A1   Apr. 22, 2010

Related U.S. Application Data

(62) Division of application No. 10/798,614, filed on Mar. 11, 2004, now Pat. No. 7,657,298.

(51) Int. Cl.
*A61B 9/00* (2006.01)

(52) U.S. Cl. .................... 600/424

(58) Field of Classification Search ............ 600/424, 600/443, 442, 440, 342, 426; 128/916
See application file for complete search history.

(56) References Cited

U.S. PATENT DOCUMENTS

| | | |
|---|---|---|
| 5,321,257 A | 6/1994 | Danisch |
| 5,441,502 A | 8/1995 | Bartlett |
| 5,558,091 A | 9/1996 | Acker et al. |
| 5,633,494 A | 5/1997 | Danisch |
| 5,665,092 A | 9/1997 | Mangiardi et al. |
| 5,917,180 A | 6/1999 | Reimer et al. |
| 6,073,043 A | 6/2000 | Schneider |
| 6,127,672 A | 10/2000 | Danisch |
| 6,338,716 B1 | 1/2002 | Hossack et al. |
| 6,356,782 B1 | 3/2002 | Sirimanne et al. |
| 6,390,982 B1 | 5/2002 | Bova et al. |
| 6,405,072 B1 | 6/2002 | Cosman |
| 6,563,107 B2 | 5/2003 | Danisch et al. |
| 6,940,062 B2 * | 9/2005 | Kwon et al. ............ 250/227.14 |
| 2004/0097807 A1 | 5/2004 | Smith et al. |

OTHER PUBLICATIONS

"Ultrasound Registration of the Bone Surface for Surgical Navigation," by Amin et al. from the Biomedical Paper, Computer Aided Surgery 8:1-16 (2003), (16 pages).

"A-Mode Ultrasound-Based Registration in Computer-Aided Surgery of the Skull," by Amstutz et al. from Arch Otolaryngol Head Neck Surg/vol. 129, Dec. 2003, (pp. 1310-1316).

* cited by examiner

*Primary Examiner* — Tse Chen
*Assistant Examiner* — Elmer Chao
(74) *Attorney, Agent, or Firm* — McCracken & Frank LLC

(57) ABSTRACT

A system is disclosed for determining a position and a change in the position of an anatomical structure. The system utilizes a surgical navigation system and a substrate that is capable of being removably mounted to an outer surface of a patient's body. The substrate includes a sensor that is tracked by the surgical navigation system and a fiber optic device that determines the position of an anatomical structure relative to the sensor. The concatenation of the position of the sensor and the relative position of the anatomical structure allows a global position of the anatomical structure to be determined by a computer system and displayed to the user.

18 Claims, 16 Drawing Sheets

US 8,082,022 B2

SYSTEM, DEVICE, AND METHOD FOR DETERMINING A POSITION OF AN OBJECT

CROSS REFERENCE TO RELATED APPLICATIONS

This application is a divisional of U.S. patent application Ser. No. 10/798,614, filed Mar. 11, 2004, the entirety of which is hereby incorporated by reference herein.

REFERENCE REGARDING FEDERALLY SPONSORED RESEARCH OR DEVELOPMENT

Not applicable

SEQUENTIAL LISTING

Not applicable

BACKGROUND

1. Technical Field

This invention relates generally to surgical navigation systems. More particularly, this invention relates to a positional device attached to a substrate that assists in determining the position and relative movement of an anatomical structure within a patient.

2. Background Art

The use of surgical navigation systems for assisting surgeons during surgery is quite common. Some systems are used to track the movement of bony structures. Determining the precise location of a bony structure, and whether it has moved, is essential when utilizing surgical instruments in fields such as orthopedic surgery. Typical surgical navigation systems utilize trackers that are rigidly attached to the underlying bony structure being monitored. Rigid attachment of navigation trackers to the bony structure is often an extremely invasive procedure that may cause additional trauma to the patient and wastes a significant amount of time. The present invention provides a system for monitoring the position and change in position of a bony structure with little or no invasiveness in a shorter amount of time.

SUMMARY OF THE INVENTION

One embodiment of the present invention is directed toward a system for determining a position and a change in the position of an anatomical structure. The system includes a surgical navigation system and a substrate including means for removably attaching the substrate to an outer surface of a body, wherein the body includes an anatomical structure. A sensor is attached to the substrate that can be tracked by the surgical navigation system to determine a position of the sensor and a fiber optic device is attached to the substrate and can be utilized to determine a position of the anatomical structure relative to the sensor, wherein the fiber optic device comprises a fiber and a means for attachment to the anatomical structure. The system further includes a first circuit for calculating a global position of the anatomical structure by concatenating the position of the sensor and the position of the anatomical structure relative to the sensor and a second circuit for displaying the global position of the anatomical structure on a display unit.

Another embodiment of the present invention is directed towards a method for determining a position and a change in the position of an anatomical structure using a surgical navigation system. The method includes the steps of providing a surgical navigation system and attaching a substrate in a removable manner to an outer surface of a body. The substrate has an associated sensor and a positional device for determining a position of the anatomical structure relative to the sensor. The positional device includes a fiber optic device attached to the substrate, the fiber optic device comprising a fiber and a means for attachment to the anatomical structure, and the body includes an anatomical structure spaced interiorly from the outer surface. The method also includes the steps of determining a position of the anatomical structure relative to the sensor using the fiber optic device and tracking the sensor with the surgical navigation system to determine a position of the sensor. Further, the method includes the steps of determining the global position of the anatomical structure by concatenating the position of the sensor and the position of the anatomical structure relative to the sensor and displaying the position of the anatomical structure on a display unit.

Other aspects and advantages of the present invention will become apparent upon consideration of the following detailed description.

DESCRIPTION OF THE PREFERRED EMBODIMENT(S)

Figure 1:
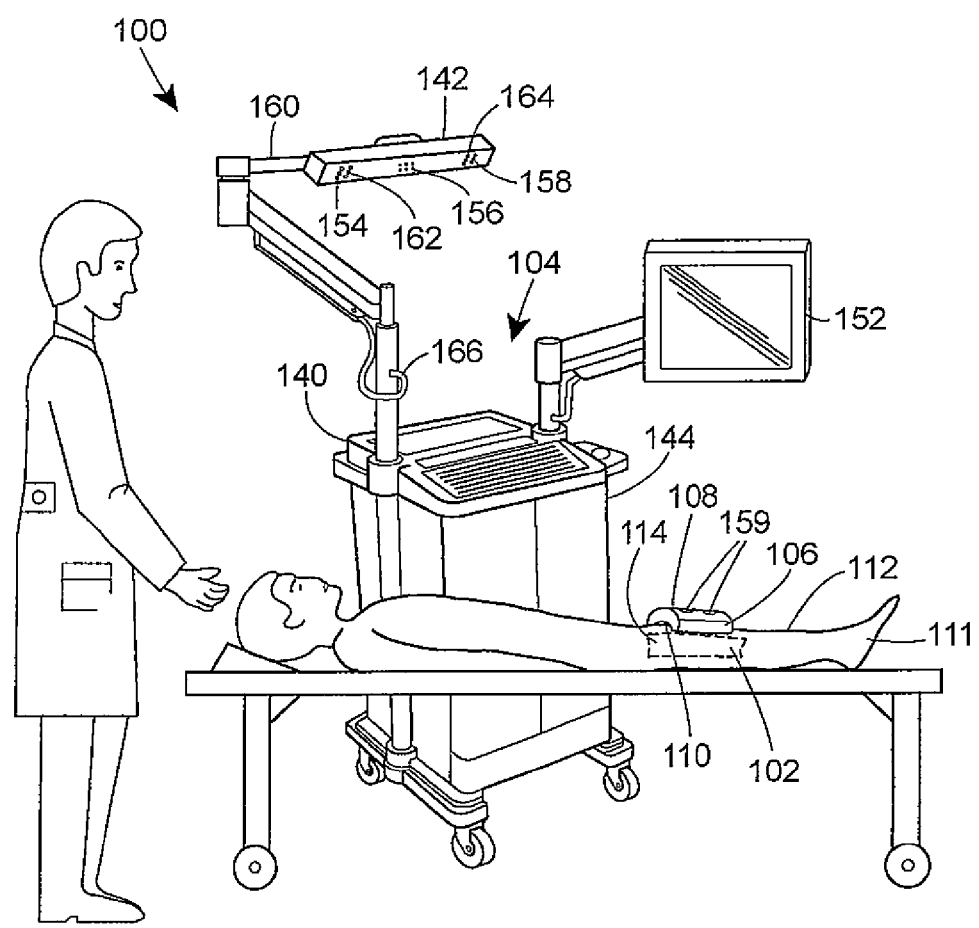
FIG. 1 is a schematic view of an embodiment of the system of the present invention.

With reference to FIG. 1, the present invention is directed toward a system 100 for determining a position and a change in the position of an anatomical structure 102. The system 100 includes a navigation system (also known as a "surgical navigation system") 104 and a substrate 106. The substrate 106 includes a sensor 108 for interacting with the navigation system 104 and a positional device 110 for determining the position of the anatomical structure 102. The substrate 106 is removably mounted to an outer surface 111 of a body 112. In a preferred embodiment of the present invention, the anatomical structure 102 found in the body 112 is a bony structure 114. However, the anatomical structure 102 may also be any organ or other structure found within the body 112 of the patient. As such, any of the embodiments hereinafter mentioned in respect to the bony structure 112 may also be used with organs or other structures that may comprise the anatomical structure 102.

The surgical navigation system 104 includes a computer system 140 and a camera array 142. The computer system 140 may be housed in a moveable cart 144. The computer system 140 may be any type of personal computer having a memory unit, a CPU, and a storage unit. A display unit 152 may also be provided, which can be any conventional display usable with a personal computer.

The camera array 142 is adapted to track the sensor 108. The camera array 142 is further adapted to transmit data between the sensor 108 and the computer system 140 representing the position of the sensor 108. In a preferred embodiment, the data is transmitted wirelessly between the sensor 108 and the computer system 140. Alternatively, a system that uses wires to transmit data between the sensor 108 and the computer system 140 can be used.

The positional device 110 is adapted to track the bony structure 114. Data from the positional device 110 represents the position of the bony structure 114 in relation to the position of the sensor 108. In a preferred embodiment, the positional device 110 is further adapted to transmit the data directly to the computer system 140. Preferably, the system will transmit the data wirelessly; however, transmission by wires can also be accomplished. In other embodiments, the data from the positional device 110 may be first communicated to the sensor 108 or camera array 142, prior to the data being sent to the computer system 140.

The camera array 142 includes a first camera 154, a second camera 156, and a third camera 158. In a preferred embodiment, the first, second and third cameras, 154, 156, and 158, are three CCD cameras adapted to detect the position of infrared signals (IR) generated by the sensor 108. In such an embodiment, the sensor 108 is an optical tracking device that comprises a plurality of LED's 159. In a preferred embodiment, the optical tracking device includes three LED's.

The camera array 142 should be mounted in a stationary position with a sufficient line of sight to the operating room. In one embodiment, the camera array 142 is mounted on a rotatable arm 160 attached to a movable stand or cart 144. In another embodiment, the camera array 142 may be mounted onto an operating room wall (not shown) or onto other convenient surfaces or locations.

At least one infrared transceiver is used to communicate data to and from the sensor 108 and/or positional device 110. In the preferred embodiment, the camera array 142 includes a first transceiver 162 and a second transceiver 164 located apart from each other. It should be noted that while both the sensor 108 and/or positional device 110 may communicate with the transceivers 162, 164 via infrared signals, those skilled in the art will realize other wireless technologies, such as those that utilize electromagnetic signals (e.g. radio frequency), may be used as well as hardwired systems. Similarly, direct communication from the positional device 110 to the computer system 140 may utilize any of these communication mediums. The camera array 142 is connected via a cable 166 to a localizer or in some instances directly to the computer system 140. The localizer cooperates with the camera array 142 to identify the location of the plurality of LED's 159 included in the sensor 108 within the line of sight of the camera array 142. In one embodiment, the localizer converts the raw position data into the position of individual LED's of the plurality of LED's 159 and transmits this information to the computer system 140. In another embodiment, the localizer converts the raw data into the position of the sensor 108 and transmits this information to the computer system 140.

The overall tracking of the bony structures 114 is achieved through concatenation of the positional data From the sensor 108 and the positional device 110. A software program in the computer system 140 can convert the raw positional data from both the sensor 108 and the positional device 110 to determine the global position of the bony structures 114. In all embodiments, the conversion of the raw data is well known to one skilled in the art and need not be further discussed.

Figure 2:
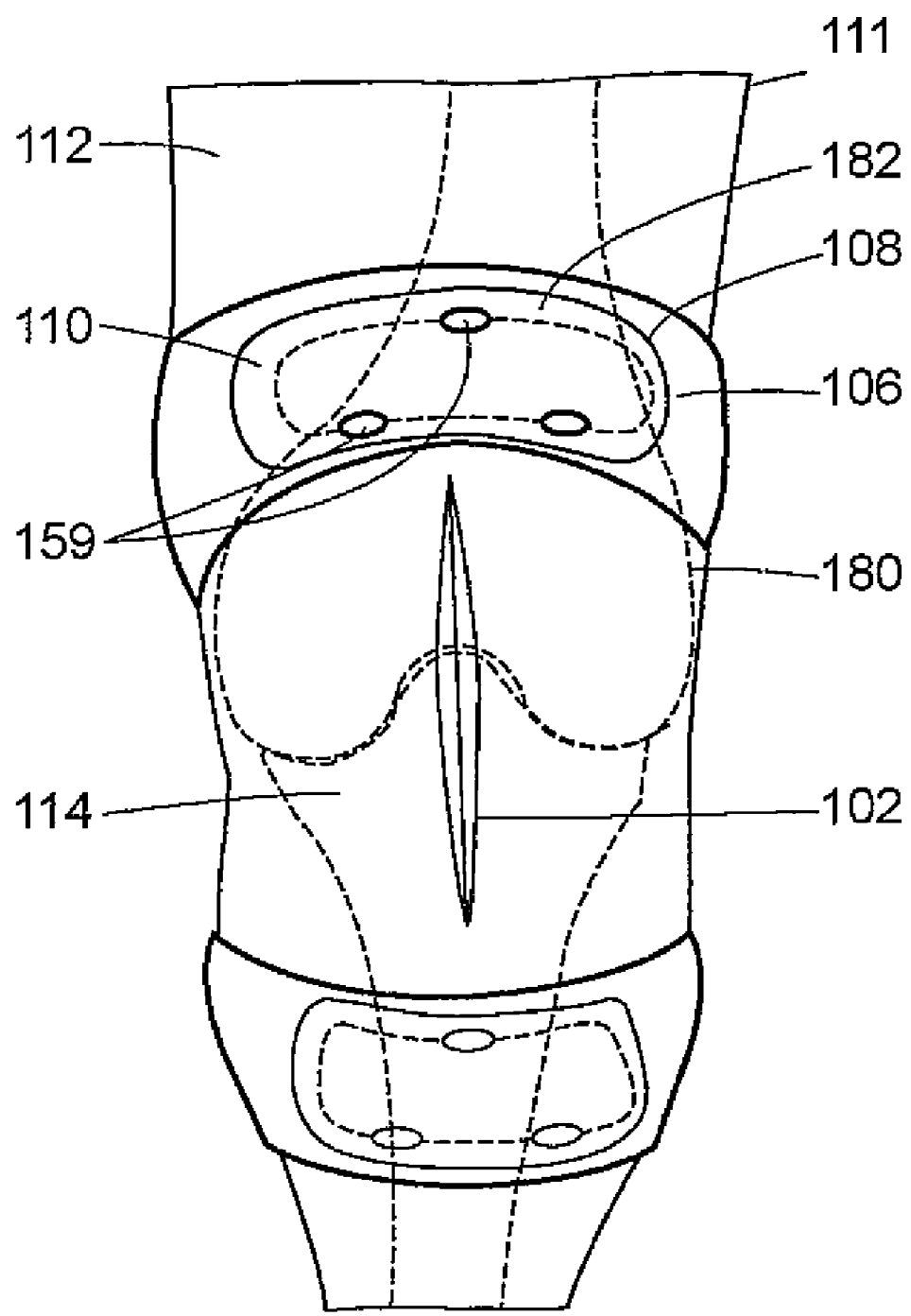
FIG. 2 is top plan view of one embodiment of a substrate with a positional device.

Preferably, the substrate 106 is capable of being removably mounted to the outer surface 111 of the body 112. The substrate of FIG. 2 includes a first side 180 and a second side 182. In a preferred embodiment, the positional device 110 is disposed on the first side 180 of the substrate 106 and the sensor 108 is disposed on the second side 182 of the substrate 106. It is also envisioned that the positional device 110 and the sensor 108 may be situated on the same side or disposed in any of a variety of positions so long as the sensor 108 can communicate with the camera array 142 and the positional device 110 can track the position of the underlying anatomical or bony structures 102, 114. Typically, the sensor 108 and the positional device 110 are in a Fixed relation. In situations where the sensor 108 and the positional device 110 are not in a fixed relation, the relationship between the two may be deduced by known methods. The substrate 106 may also take on a variety of forms dependent on the user's needs and/or the type of positional device 110 used. In one embodiment, the substrate 106 is made of a flexible material that will not interfere with ultrasound waves. In another embodiment, the substrate 106 is formed from polyester and similar materials that will not interfere with magnetic fields. In one particular embodiment, the substrate is about 5 cm in length and about 5 cm in width. The substrate 106 may be mounted to the outer surface 111 of the body 112 by an adhesive material, a band, or any other suitable attachment means presently used in conventional surgical operations.

Figure 3:
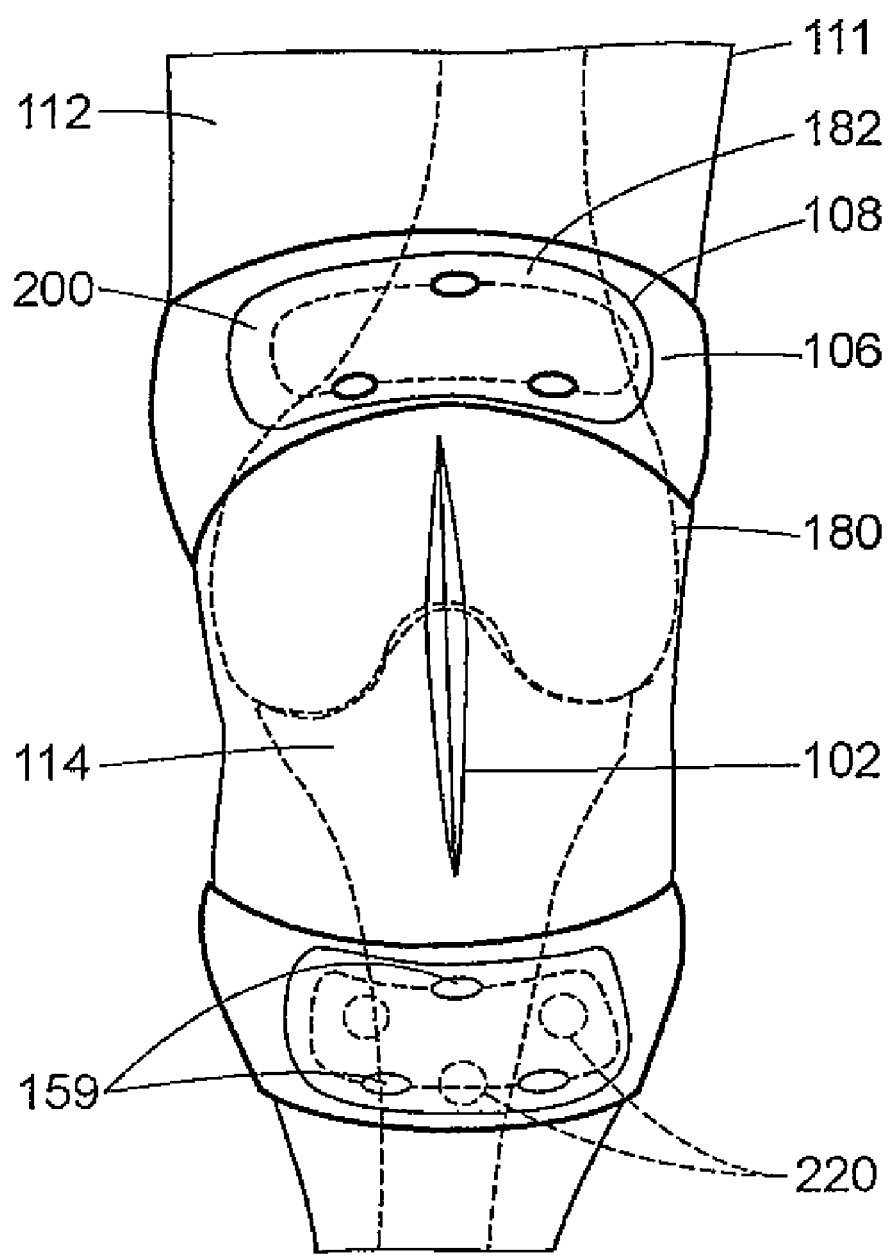
FIG. 3 is a top plan view of an embodiment similar to the one seen in FIG. 2 with an ultrasonic imaging device.

As shown in FIG. 3, the positional device 110 is an ultrasonic imaging device 200. Ultrasonic imaging devices 200, such as those used in U.S. Pat. No. 6,390,982 and U.S. Pat. No. 6,338,716 that are hereinafter incorporated by reference, are well known in the art. The ultrasonic imaging device 200 is disposed on the first side 180 of the substrate 106 while the sensor 108 is attached to the second side 182 of the substrate 106. By concatenating the positional data from the ultrasonic imaging device 200 and the positional data from the sensor 108, the global position and global change in position of the bony structures 114 may be calculated and displayed. The present embodiment has the added advantage of allowing the global position of the bony structure 114 to be determined without having a priori knowledge of the bony structure 114. Therefore, in one embodiment an image of the bony structure 114 is not needed to determine the global position. If used, the image could be a pre-operative image, an intra-operative image, or any other image typically used in surgical procedures.

The ultrasonic imaging device 200 allows the user to track the position of an underlying bony structure 114 without the need to invasively fix a tracking device to the body 112. The ultrasonic imaging device 200 comprises at least three ultrasound transducers 220. The ultrasound transducers 220 are made up of several piezoelectric elements that may be arranged separately or combined as desired. Multiple piezoelectric elements are sometimes arranged in patterns in a common housing, these are usually linear, matrix or annular in shape. The elements may be pulsed simultaneously, or the elements may be pulsed in a certain pattern to each other.

In the present embodiment, the ultrasound transducers 220 are disposed on the first side 180 of the substrate 106. The plurality of LED's 159 included in the sensor 108 are disposed on the second side 182 of the substrate 106. Positional data garnered from the ultrasound transducers 220 relates the position of the underlying bony structure 114 to the sensor 108. The knowledge of the relationship between the sensor 108 and the ultrasound transducers 220 will typically be known, but may be deduced from the shape described by the sensor 108 if the relationship is unknown or non-constant. The computer system 140 calculates the global position of the bony structure 114 by concatenating the position of the sensor 104 and the relative position of the bony structure 114 to the sensor 108.

In one embodiment, the ultrasonic imaging device 200 is initialized by first mapping a sub-area of the bony structure 114 covered by the device. It may be necessary to apply a slight motion to the ultrasonic imaging device 200 to create differential distance maps of the bony structure 114 in order to discard discrepancies. By considering numerous distance maps of the static and moving ultrasonic imaging device 200, the data can be correlated so that an arbitrary initial distance map can be established. Further, this embodiment will also establish an arbitrary transformation between the bony structure 114 coordinates and the sensor 108 so as to establish a position of the bony structure 114 in relation to the sensor 108. As mentioned before, the positional data from the bony structure 114 and the sensor 108 will then be concatenated to determine the global position of the bony structure 114.

By constantly mapping the bony structure 114 and comparing the data with the arbitrary initial position, the relative movement of the bony structure 114 can be determined and relayed to the user. The distance map produced may be a three dimensional or two dimensional distance map. In either scenario, the navigational system 104 or ultrasonic imaging device 200 will still track the underlying bony structure 114 and correlate this information with the initial bony structures 114 position to determine if the position of the bony structure 114 has changed and/or to supplement the initial position data. Additionally, as more positional data of the bony structure 114 is accumulated, the initial distance map will grow to include missing data.

In order to increase tracking accuracy, some embodiments utilize multiple ultrasonic imaging devices 200 and sensors 108 to track the bony structure 114. Such coupled trackers can be distributed radially or axially over larger areas of the outer surface of the patient to cover distant portions of the same bony structure 114. By utilizing multiple coupled trackers, and taking into consideration the relative position of the coupled trackers to each other, the captured information per unit can be decreased without loss of accuracy. The coupled trackers may be calibrated by temporarily introducing a known calibration object (not shown) into the surrounding tissue of the patient's body. In some embodiments, the calibration object is disposed within the tissue of the patient at a known distance from the coupled trackers. In instances where the calibration object is disposed an unknown distance from the coupled trackers, the calibration object can be used to determine the relative distances between the coupled trackers. In one embodiment, the calibration object is a thin translucent needle with an ultrasonic tip.

The ultrasonic imaging device 200 of the last embodiment may be utilized along with passive point sources to aid in the positioning of the bony structure 114. At least three passive point sources must be used. It is also envisioned that multiple ultrasonic imaging devices 200 may be used in a similar manner as discussed above, including the calibration techniques expounded upon. In the embodiment depicted in FIG. 4, four sonic reflective balls (passive point sources) 240a, 240b, 240c, 240d are percutaneously injected under the transducers 242a, 242b, 242c, 242d and disposed adjacent the bony structure 114. Because the sonic reflective balls 240a-d lie adjacent the bony structure 114, the determination of the position of the sonic reflective balls 240a-d will indicate the position of the bony structure 114. The transducers 242a-d are equivalent to the transducers 220 discussed above. The sonic reflective balls 240a-d may be substantially comprised of air or comprised of other low density or high density materials. Sonic reflective balls 240a-d made of high density materials could utilize materials such as gold and platinum that have good reflective properties. Sonic reflective balls 240a-d made of low density materials may be formed from resorbable materials. Sonic reflective balls 240a-d composed of resorbable material will allow the balls to be absorbed within the patient after the procedure has been completed. In one embodiment, the sonic reflective balls 240a-d comprise a thin outer shell formed of resorbable material with an inner core substantially comprised of air. Those skilled in the art will know what materials may be considered resorbable within the context of the present embodiments.

The position of the sonic reflective balls 240a-d relative to the sensor 108 is determined by the transducers 242a-d. As noted before, there is a known relationship between the transducers 242a-d and the sensor 108. During the positioning process, one transducer is activated at a time. While any of the transducers 242a-d can send out the initial ultrasonic pulse, for illustrative purposes transducer 242a has been marked as a sending transducer. The sending transducer 242a emits an ultrasonic pulse toward the bony structure 114, which is reflected off of the sonic reflective ball 240a. All of the transducers 242a-d receive the sound wave reflected from the sonic reflective ball 240a. The length of the path from the sending transducer 242a to the sonic reflective ball 240a to the receiving transducers 242a-d is a function of the time between when the ultrasound pulse was first emitted and then later received by each of the receiving transducers 242a-d. All of the sonic reflective balls 240a-d positions can be determined by activating the respective transducer 242a-d above the sonic reflective balls 240a-d one at a time. Those skilled in the art will know how to determine the position of the bony structure 114 in relation to the sensor 108 from the data provided by the transducers 242a-d and the known distance between the transducers 242a-d and the sensor 108.

Figure 4:
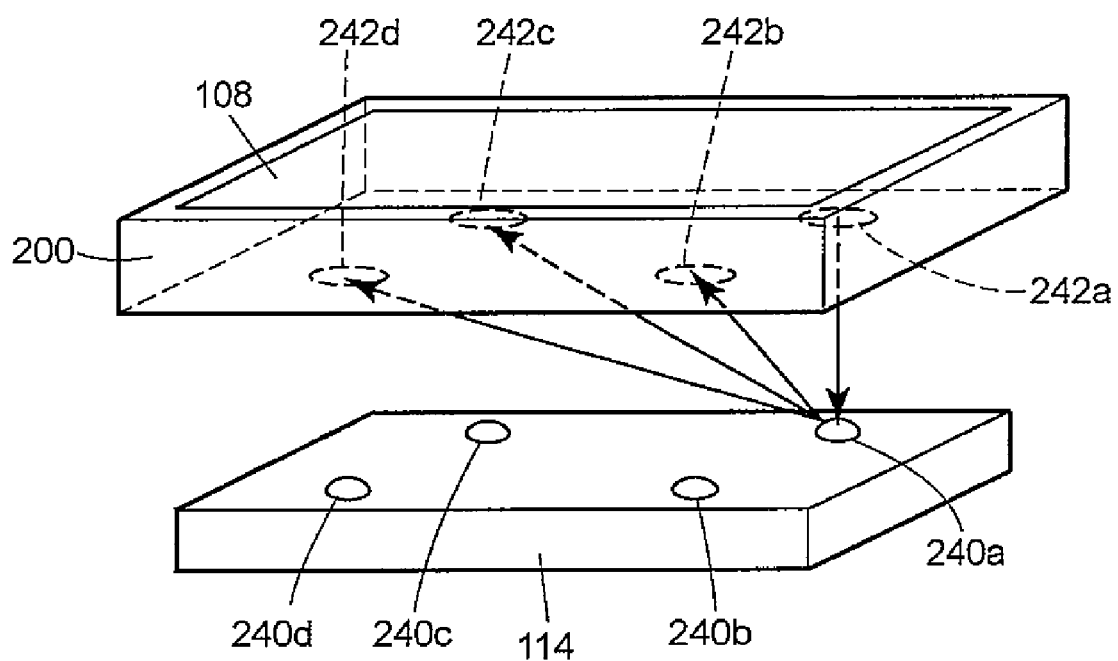
FIG. 4 is an isometric view of a further embodiment of the present invention utilizing an ultrasonic imaging device.
Figure 5:
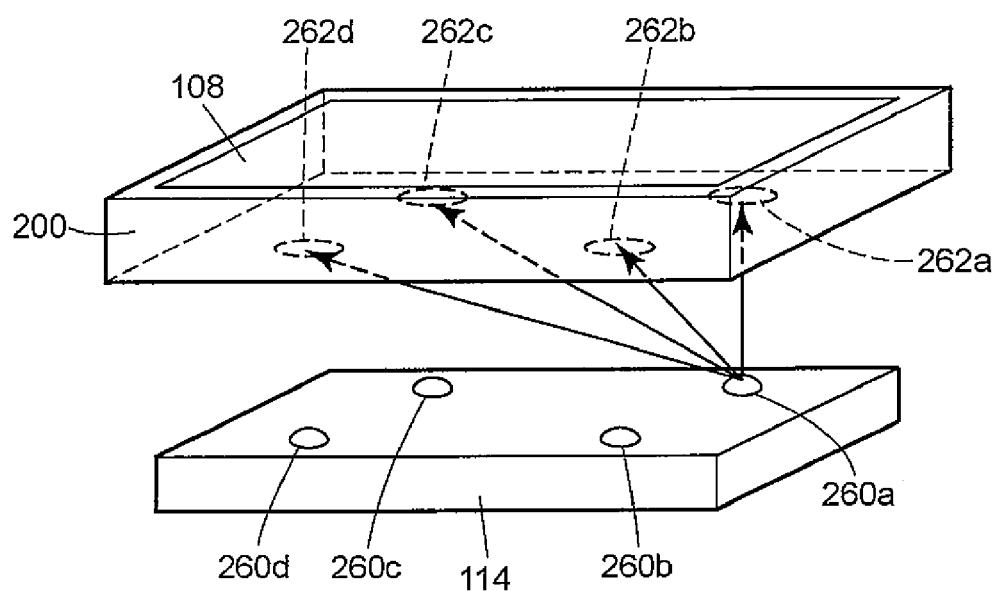
FIG. 5 is an isometric view of another embodiment of the present invention utilizing an ultrasonic imaging device.

FIG. 5 shows the ultrasonic imaging device 200 of the embodiment of FIG. 4 modified to utilize active point ultrasonic sources as opposed to passive point sources. At least three active point transducers must be inserted into the tissue under three respective receivers. Similar to the prior embodiments, multiple ultrasonic imaging devices 200 and corresponding calibration techniques may be utilized. In the present embodiment illustrated in FIG. 5, four active point ultrasonic transducers 260a, 260b, 260c, 260d are disposed adjacent the bony structure 114 in a similar manner as the sonic reflective balls 240a-d in the last embodiment. Additionally, four receivers 262a, 262b, 262c, 262d are disposed on the first side 180 of the substrate 106, wherein the transducers 262a-d are in a known relationship with the sensor 108.

Similar to the prior embodiment, the position of active point ultrasonic transducers 260a-d relative to the sensor 108 is determined by the receivers 262a-d. During the positioning process, one of the active source ultrasonic transducers 260a-d is activated at a time. To illustrate the present embodiment, active source ultrasonic transducer 260a has been labeled a sending active source transducer. The sending active source ultrasonic transducer 260a emits an ultrasonic pulse in all directions, which is received by all of the receivers 262a-d. Based on the time between the emission of the ultrasonic pulse from the sending active source transducer 262a and the time the pulse was received by each respective receiver 262a-d, the length of the path between the sending active source transducer 262a and each respective receiver 262a-d can be determined. Those skilled in the art will know how to determine the position of the bony structure 114 in relation to the sensor 108 from the data provided by the receivers 262a-d and the known distance between the transducers 262a-d and the sensor 108.

With respect to all the embodiments mentioned above, it is envisioned that some embodiments may use a single substrate 106 while others will use multiple substrates 106. As long as at least one transducer 220, transducer 242a-d, or receiver 262a-d is included within the ultrasonic imaging device 200 on each substrate 106, those skilled in the art will know how to translate the positional data for each respective substrate 106 into a global position of the bony structure 114. The substrates 106 used in the present embodiments could be attached by an ultrasonic coupling adhesive known to those in the art to the outer surface 111 of the body 112. Additionally, the generally flexible nature of the substrate 106 will not pose a problem, as the relationship of the transducers 220, transducers 242a-d, and receivers 262a-d to each other and the bony structure 114 need not be fixed at all times. In some embodiments, measurements are taken every 10 milliseconds, obviating the need for a more rigid structure for the substrate 106. Also, the above embodiments have been described using four ultrasound transducers and four ultrasound receivers. It is also possible to use three ultrasound transducers and/or receivers and achieve similar results.

Figure 6A:
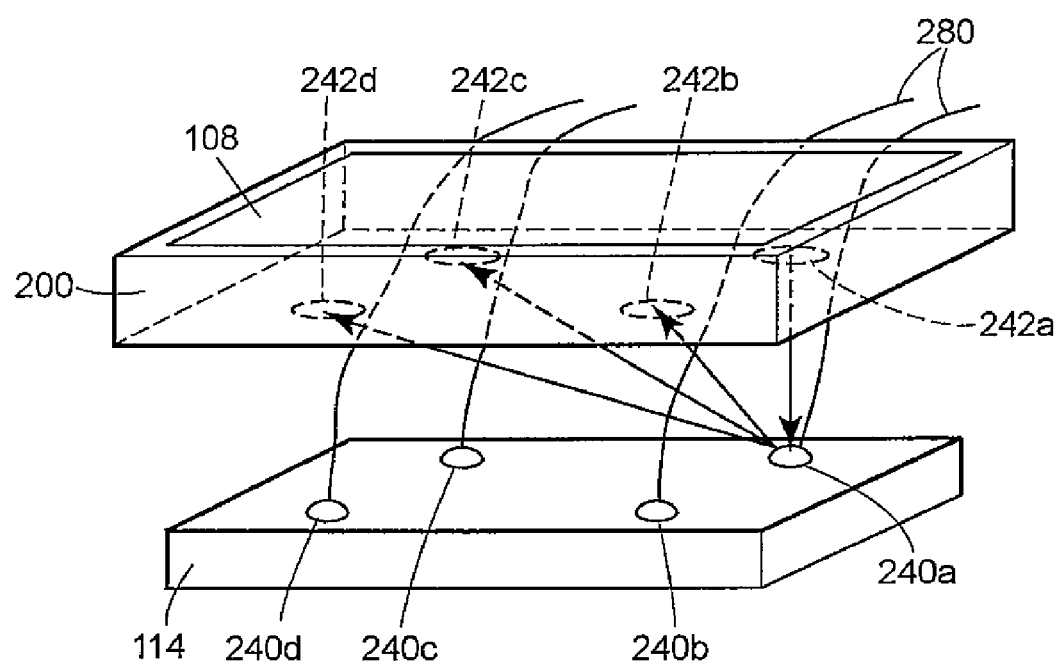
FIG. 6*a* is another isometric view of the embodiment in FIG. 4 with a removal device shown.
Figure 6B:
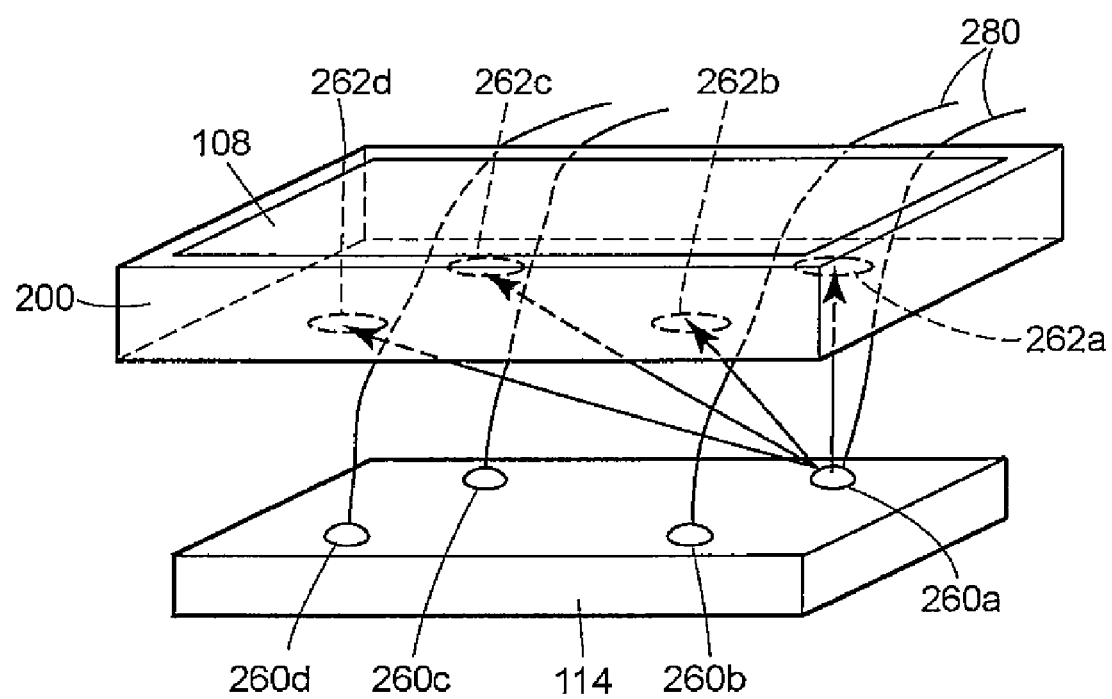
FIG. 6*b* is another isometric view of the embodiment in FIG. 5 with a removal device shown.

The advantages of utilizing an ultrasonic imaging device 200 are easily seen in patient comfort and User convenience. There is no need for the surgeon to make further incisions on the patient's body 112 to accommodate the ultrasonic imaging device 200 or further traumatize the region undergoing surgery. While a completely non-intrusive embodiment has been disclosed, even the other embodiments utilizing active and passive point sources are relatively non-invasive. Nothing needs to be screwed into the bony structure 114, as the sonic reflective balls 240a-d and the active source transducers 260a-d are merely disposed adjacent the bony structure 114. Additionally, as may be seen in FIGS. 6a and 6b, the sonic reflective balls 240a-d and the active source transducers 260a-d, respectively, may have a removal device 280 attached to them. The removal device 280 may be a wire or any other analogous removal mechanism that allows for convenient removal of the sonic reflective balls 240a-d and active source transducers 260a-d from the body 112 of the patient. The relatively non-invasive embodiments of the present invention will allow the patient to heal faster and reduce the chance of infection or other complications from a more invasive procedure.

Figure 7:
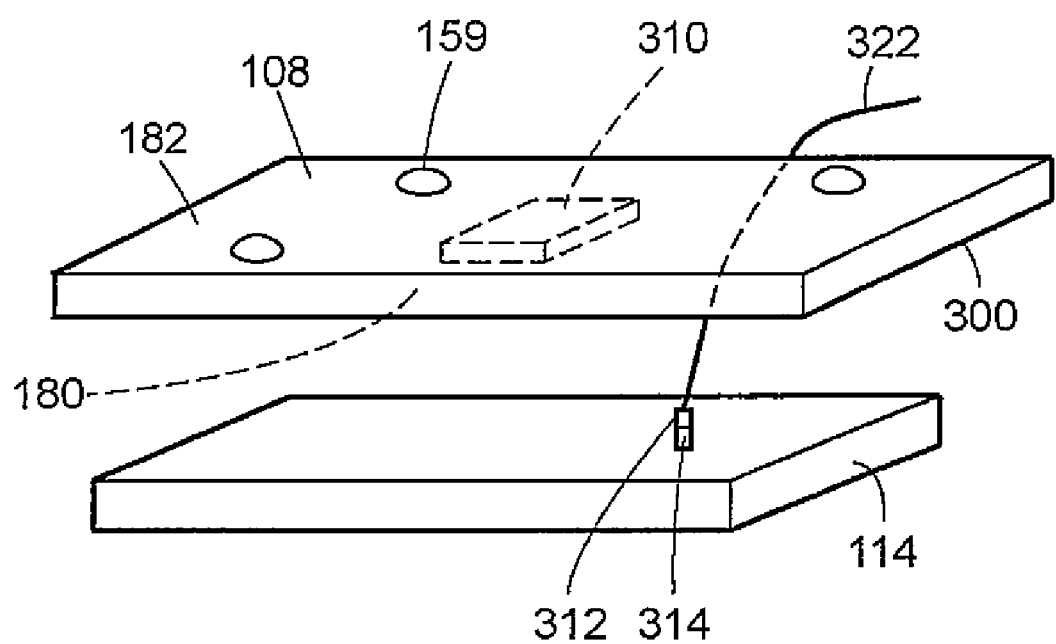
FIG. 7 is an isometric view of a still further embodiment of the present invention utilizing a magnetic tracker.

FIG. 7 shows another embodiment of the present invention, wherein the positional device 110 is a magnetic tracker 300. Magnetic tracking devices and localization systems such as those taught in U.S. Pat. No. 6,073,043, which is hereinafter incorporated by reference, have been used with limited success in the past. The present embodiment disposes the magnetic tracker 300 on the first side 180 of the substrate 106 while disposing the sensor 108 on the second side 182 of the substrate 106. Similar combinations and orientations of the removably mounted substrates 108 as discussed above may be used. It is also envisioned that any of the embodiments related to the sensor 108 and the surgical navigation system 104 discussed above may be used in the present embodiment.

Figure 8:
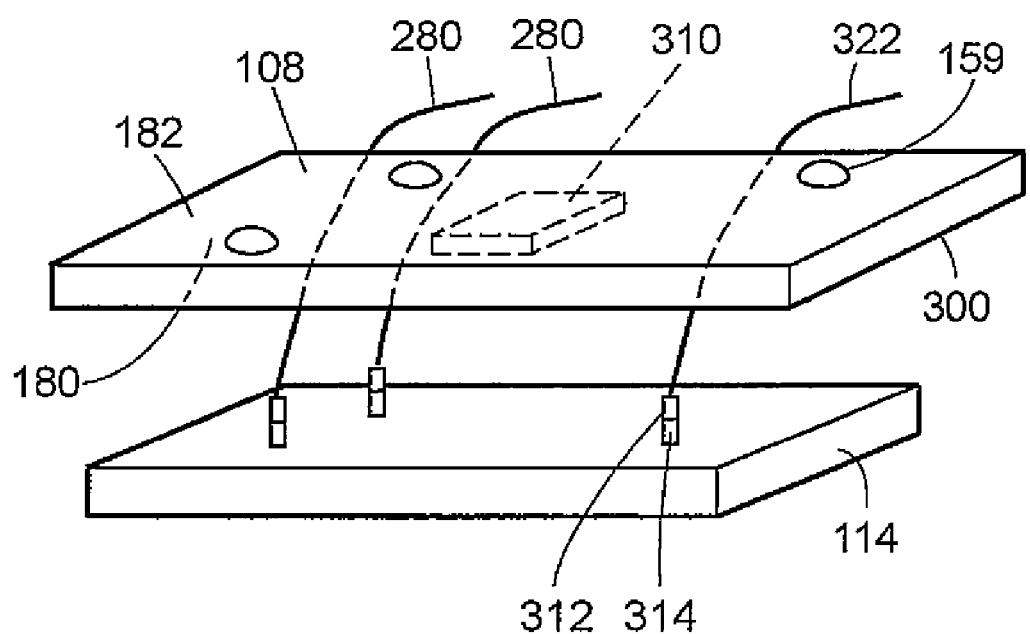
FIG. 8 is an isometric view of yet another embodiment of the present invention utilizing a magnetic tracker.

The magnetic tracker 300 of the present embodiment comprises a magnetic transmitter 310 and a magnetic sensor 312. The magnetic transmitter 310 is disposed on the substrate 106, while the magnetic sensor 312 is disposed beneath the magnetic transmitter 310 and is rigidly attached to the bony structure 114. The magnetic sensor 312 includes an anchor 314 for attaching the magnetic sensor 312 to the bony structure 114. It is envisioned that the term anchor 314 encompasses pins, screws, nails, or any other attachment device known to those in the art. In some embodiments, a plurality of magnetic sensors 312 are provided that work with the magnetic transmitter 310, as may be seen in FIG. 8. The magnetic transmitter 310 contains magnetic field generators that can determine the position of the magnetic sensor 312, and thus the bony structure 114, in relation to the sensor 108. By concatenating the positional data from the magnetic tracker 300 and the positional data from the sensor 108, the global position and global change in position of the bony structure 114 may be calculated and displayed.

Figure 9:
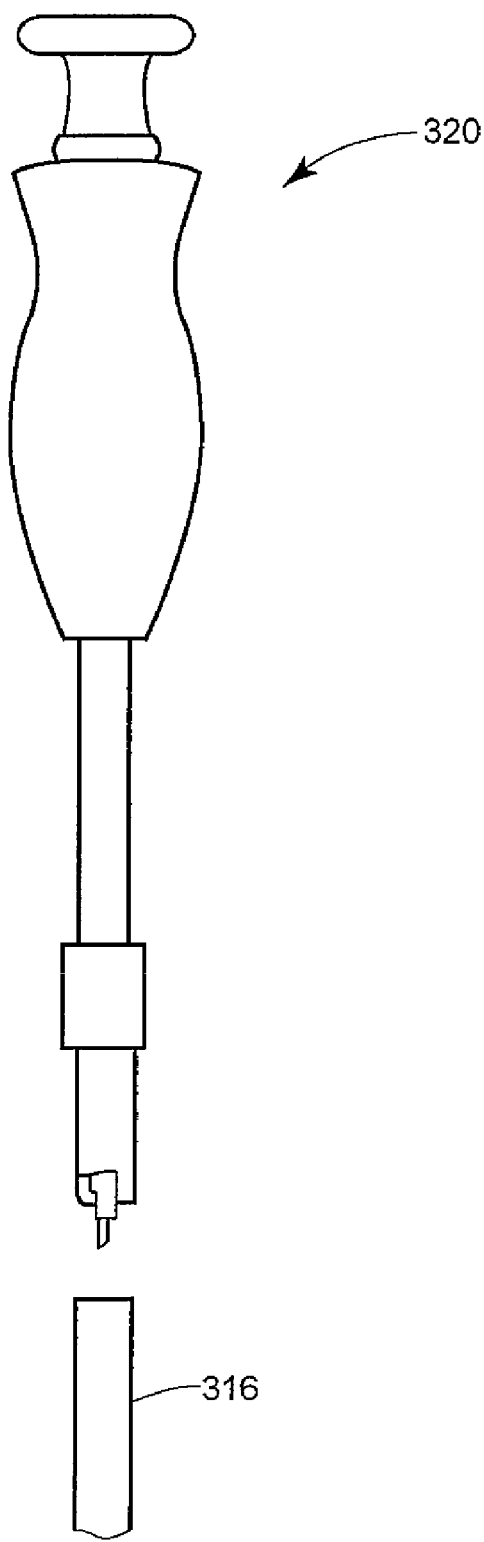
FIG. 9 is a side elevational view of an impaction device suitable for use in an embodiment of the present invention.

In a preferred embodiment, the anchor 314 is introduced in a one step process transcutaneously through a sleeve 316 with an integrated impaction device 320, as seen in FIG. 9 or as those taught in U.S. Pat. No. 5,665,092, which is hereinafter incorporated by reference. For intra-operative access, the sleeve 316 can be affixed to the anchor 314 in order to create an access tunnel that will not interfere with the surrounding tissue. In addition, or alternatively, a retrieval device 322 is connected to the sensor 108. The retrieval device 322 may comprise a guide wire or guide fiber to facilitate penetration through the tissue of the body 112 and/or for extraction of the magnetic sensor 312 after the user is finished. In some embodiments, the retrieval device 322 is attached to the first side 180 where the magnetic tracker 300 is disposed.

Figure 10:
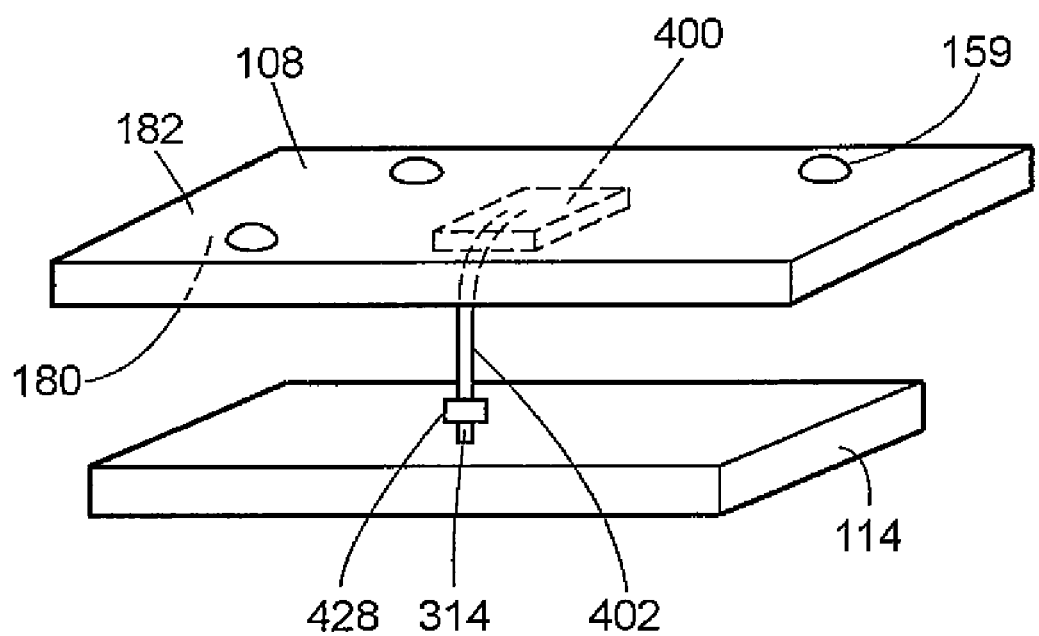
FIG. 10 is an isometric view of an additional embodiment of the present invention utilizing a fiber optic device.

FIG. 10 shows yet another embodiment, wherein the positional device 110 is a fiber optic device 400. Fiber optic devices, such as those found in U.S. Pat. No. 5,633,494 and U.S. Pat. No. 6,127,672, are well known in the art and are herein incorporated by reference. Any of the prior embodiments pertaining to the surgical navigation system 104, the substrate 106, the sensor 108, or any other structure utilized with the ultrasonic imaging device 200 and the magnetic tracker 300 may be used in the present embodiments.

The fiber optic device 400 is disposed on the first side 180 of the substrate 106, while the sensor 108 is disposed on the second side 182. The fiber optic device 400 includes a non-rigid tubular attachment 402 of known length that has at least one fiber 404. In a preferred embodiment, the fiber 404 is a light conducting fiber commonly known as a fiber optic wire. The tubular attachment 402 extends from the fiber optic device 400 to the anchor 314 that can be removably attached to the bony structure 114. The tubular attachment 402 may also act as a penetration device for guiding the anchor 314 through the tissue of the body 112 and as a retrieval device for aiding in extracting the anchor 314 after the user is finished. Any of the structure or methods used to attach and remove the anchors 314 in the embodiments utilizing the magnetic trackers 300 may also be used in the present embodiments. Bending of the fiber 404 within the tubular attachment 402 corresponds to the position of the anchor 314. The fiber optic device 400 can use the positional data of the anchor 314 to relay where the bony structure 114 is in relation to the sensor 108.

Figure 11:
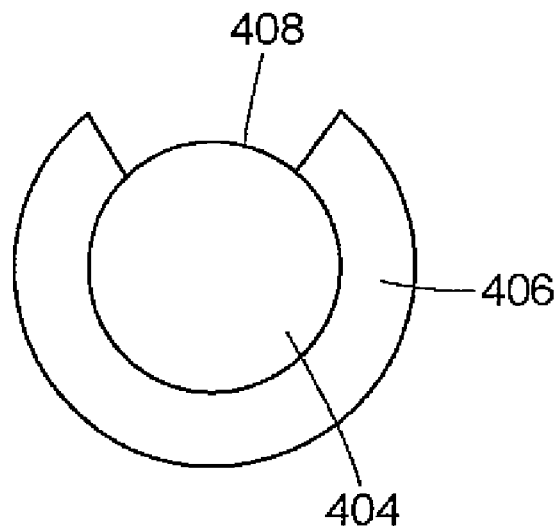
FIG. 11 is a cross section of a fiber suitable for use in the device of FIG. 10.
Figure 12:
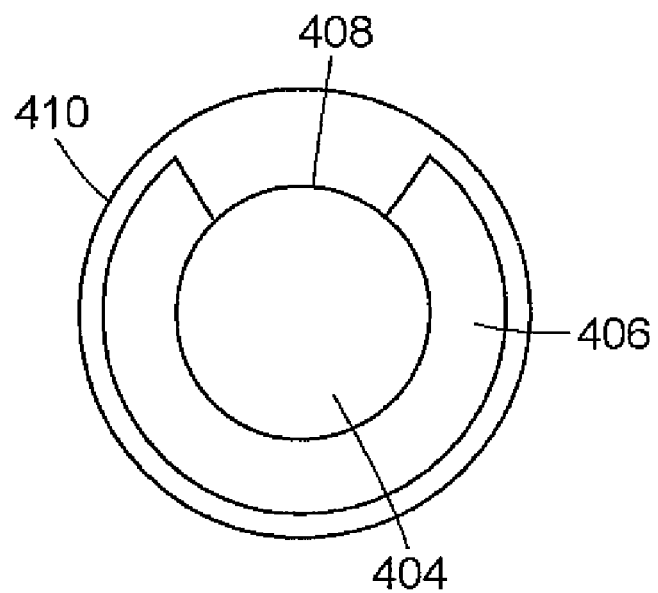
FIG. 12 is a cross section of a fiber similar to FIG. 11.

FIG. 11 illustrates a cross sectional view of the fiber 404. The fiber 404 usually includes a cladding 406 surrounding the length of the fiber 404. In the present embodiment, a bending sensor 408 is created by removing the cladding 406 from around a portion of the fiber 404 and/or serrating the underlying portion. In one embodiment depicted in FIG. 12, the bending sensor 408 may be treated with a light absorbent material 410 to prevent light from being reflected back into the bending sensor 408. The light absorbent material may serve other purposes as well, such as protecting the fiber against environmental contamination. One skilled in the art will know how to create the bending sensor 408 and what materials to use for the light absorbent material 410.

Figure 13:
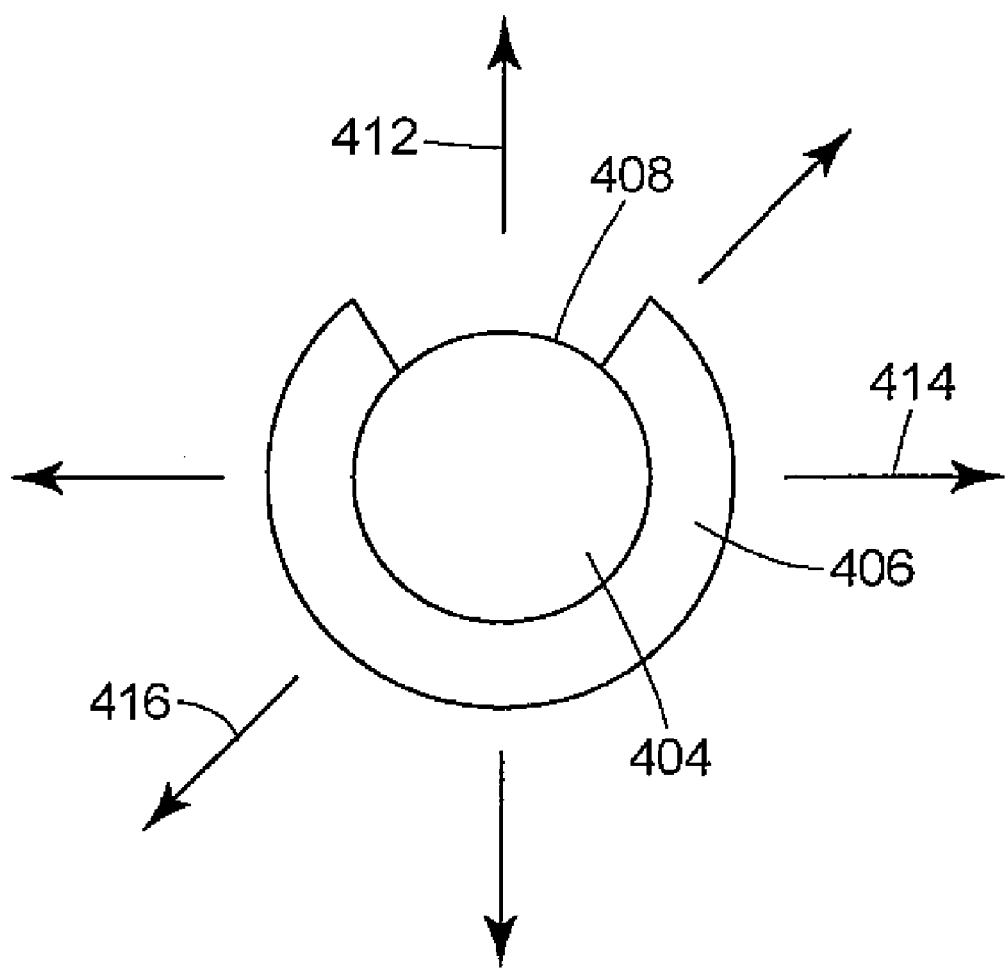
FIG. 13 is a cross section of a fiber showing axes of sensitivity for a bend sensor.

The fiber optic device 400 utilizes photo detectors to determine the amount of light lost over the serrated portion comprising the bending sensor 408. The modulation in intensity of the light traveling through the fiber 404 is linear with the curvature of the fiber 404. Therefore, the amount of light lost through the bending sensor 408 is a function of the position of the anchor 314. FIG. 13 depicts a fiber 404 with a bending sensor 408 located on a side of the fiber 404. A vertical plane 412 transmits the greatest amount of light when bent. If the fiber 412 is bent concave upward along the vertical plane 412, the transmission increases. If the fiber 404 is bent concave downward, the transmission decreases. A horizontal plane 414 corresponds with the least amount of light being lost when bent along this plane 414. Intermediate responses occur on planes not lying within the aforementioned two planes, such as a plane 416.

One embodiment of the present invention allows the fiber 404 to extend from the portion of the fiber optic device 400 disposed on the first side 180 of the substrate 106 to the anchor 314 that is removably attached to the bony structure 114 and back to the fiber optic device 400. The single fiber 404 includes one bending sensor 408 disposed at an end of a loop formed by the fiber 404 between the photo detectors and the end of the loop disposed on the anchor 314. In an alternative embodiment depicted in FIG. 14, the loop of fiber 404 formed near the anchor 314 is eliminated by first and second fibers 418, 420, respectively. Light from a sending photo detector 422 is sent through a bending sensor 408 to a first end 424 of the first fiber 418. The first end 424 includes a first sensing portion 426 that faces a second sensing portion 428 at the second end 430 of the second fiber 420. The two sensing portions 426, 428 include non-cladded and/or serrated portions to allow for light transfer. Light from the second fiber 420 is then transmitted to a retrieving photo detector 432. A cap 434 or other covering mechanism covers the sensing portions 426, 428 and holds them in a rigid fashion so that they do not bend. The cap 434 may be disposed adjacent or within the anchor 314. This arrangement allows the first and second fibers 418, 420 that run parallel to each other to perform the same function without a looped end. An added advantage is that such an arrangement allows for the bending sensors 408 to be placed in more narrow structures, which is particularly advantageous for surgical procedures that want to minimize the invasiveness of the procedure. One skilled in the art will realize there are numerous ways to utilize looped or non-looped fibers to convey bending, particularly in the manner in which light is transmitted from the first fiber 418 to the second fiber 420 in non-looped systems.

Figure 14:
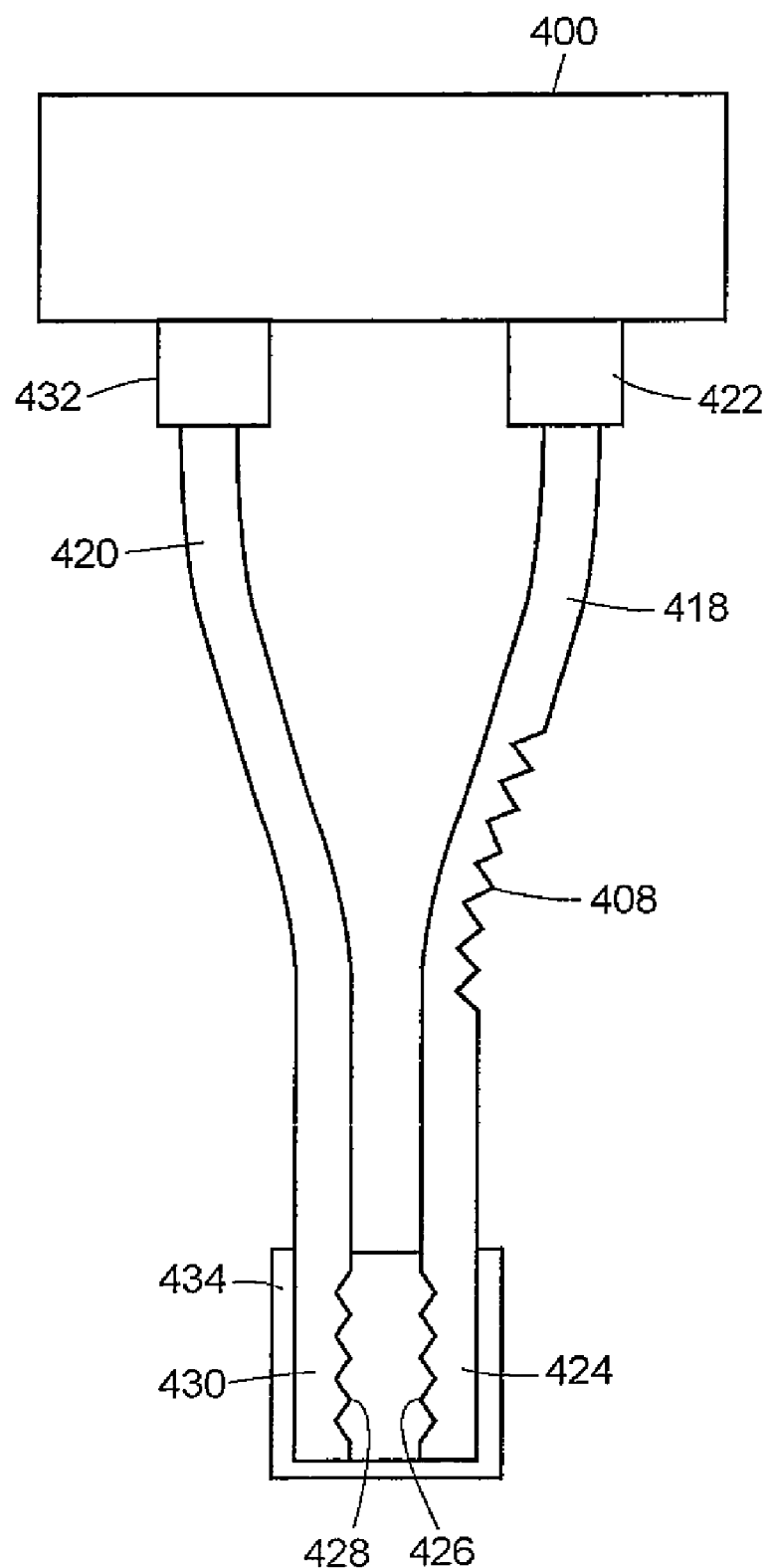
FIG. 14 is an embodiment of the fiber optic device that shows how light is transmitted between fibers.
Figure 15:
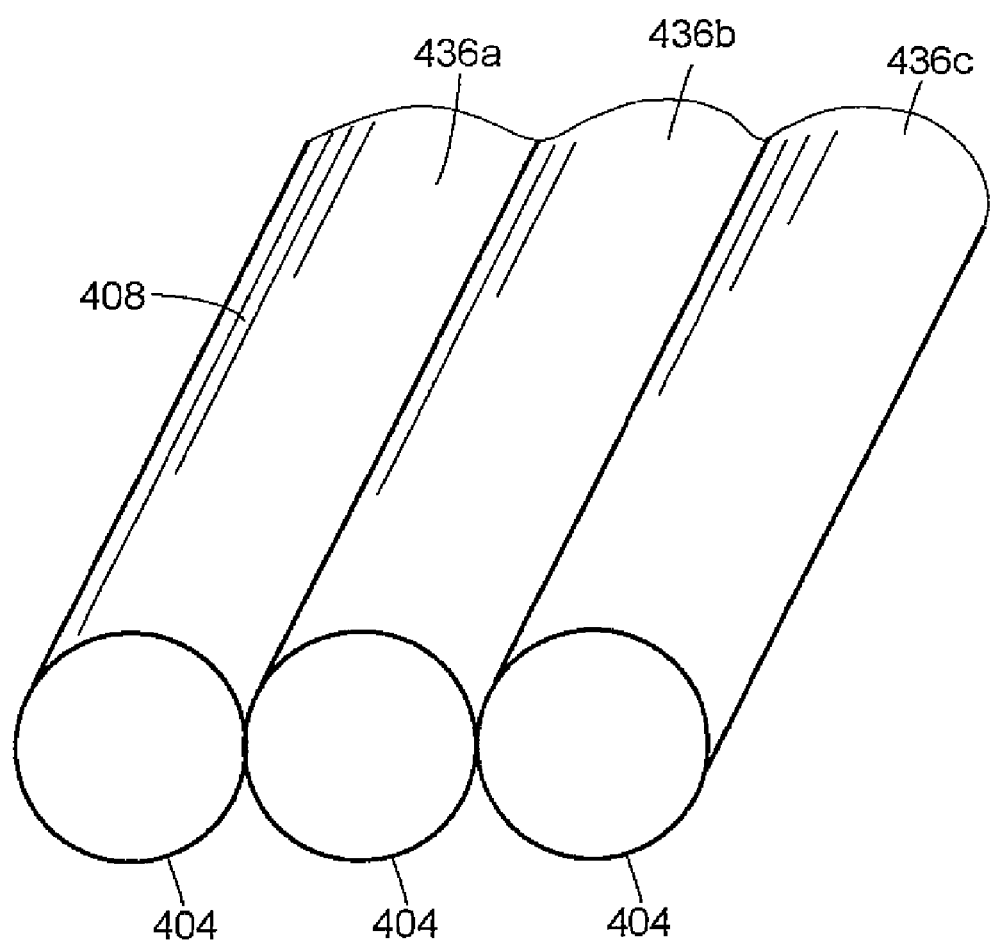
FIG. 15 is a perspective view of three fibers with bending sensors disposed on different areas of each respective fiber.

In other embodiments of the present invention multiple fibers 404 may be used as opposed to the one or two discussed above. FIG. 15 shows a preferred embodiment wherein three fibers 436a, 436b, 436c are placed parallel to each other. Each fiber 404 has a bending sensor 408 that will relay different bending vector components. The bending sensors 408 are arranged to allow for the axes of maximum light transmission to be 120 degrees from each other. The three fibers 436a, 436b, 436c are correspondingly coupled with three other fibers (not shown) in a similar arrangement as seen in FIG. 14. The three fibers 436a, 436b, 436c each have an end that corresponds with respective ends of the other three fibers. This embodiment allows for a relatively narrow structure to be used while also receiving three bending vector components. The three bending vector components are beneficial in calculating a more accurate positioning of the anchor 314 as opposed to single or two fiber systems. It is envisioned that a plurality of different numbers and arrangements of fibers 404 may be used in different embodiments.

Figure 16:
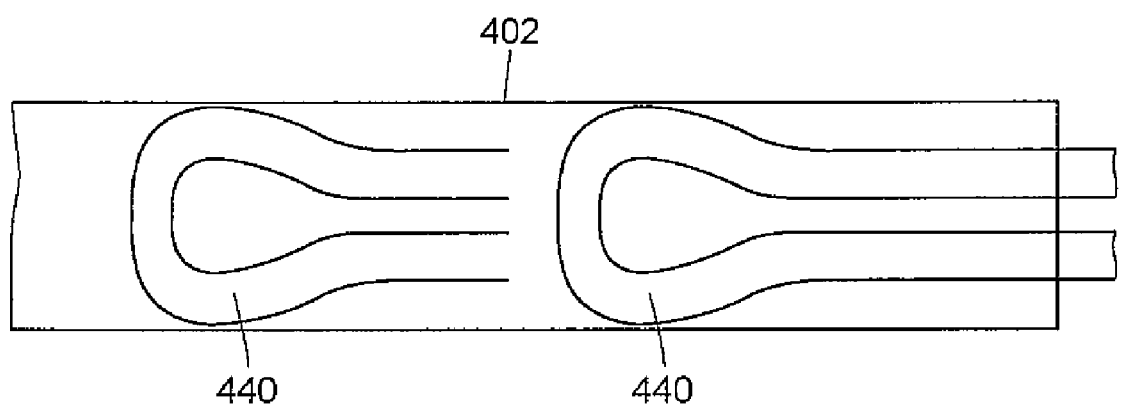
FIG. 16 is a further embodiment of a fiber optic device using a series of looped sensors.

The number or bending sensors 408 provided within the tubular attachment 402 may also vary. FIG. 16 shows a series of bending sensors comprising looped fibers disposed within the tubular attachment mechanism. By providing a series of looped sensors 440, numerous positional determinations may be taken that can be combined to realize a more accurate position of the anchor 314 relative to the sensor 108. One skilled in the art will realize that numerous combinations and types of fiber arrangements exist that provide for multiple bending sensors 408 along the length of a material.

In all embodiments utilizing the fiber optic device 400, data is received by the fiber optic device 400 corresponding to the position of the anchor 314 attached to the bony structure 114. As mentioned before, there is also a known relationship between the sensor 108 and the fiber optic device 400 on the substrate 106. Data corresponding to the position of the bony structure 114 relative to the sensor 108 is relayed by the fiber optic device 400 in a manner similar to the other embodiments discussed above.

INDUSTRIAL APPLICABILITY

The methods and systems disclosed herein assists in determining a position and relative movement of an anatomical structure within a patient.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:
1. A system for determining a position and a change in the position of an anatomical structure, comprising:
   a surgical navigation system;
   a substrate including means for removably attaching the substrate to an outer surface of a body, wherein the body includes an anatomical structure;
   a sensor attached to the substrate that can be tracked by the surgical navigation system to determine a position of the sensor;
   a fiber optic device attached to the substrate utilized to determine a position of the anatomical structure relative to the sensor, wherein the fiber optic device comprises a fiber and a means for attachment to the anatomical structure;

a first circuit for calculating a global position of the anatomical structure by concatenating the position of the sensor and the position of the anatomical structure relative to the sensor; and a second circuit for displaying the global position of the anatomical structure on a display unit.

2. The system of claim 1, wherein multiple fiber optic devices simultaneously track the position of the anatomical structure.

3. The system of claim 1, wherein the fiber includes a serrated portion for the emission of light along a length of the fiber.

4. The system of claim 3, wherein the serrated portion is covered by a light absorbent material.

5. The system of claim 1, wherein the means for attachment comprises a pin that is adapted to be removably attached to the anatomical structure, and wherein the fiber is attached to the pin.

6. The system of claim 1, wherein the fiber optic device is connected to a retrieval device.

7. The system of claim 6, wherein the retrieval device comprises a wire.

8. The system of claim 6, wherein the retrieval device comprises a tubular attachment.

9. The system of claim 6, wherein the retrieval device is attached to the substrate.

10. The system of claim 1, wherein the anatomical structure is a bony structure, the sensor comprises an optical tracking device, and the substrate is approximately 5 cm in width and approximately 5 cm in length.

11. The system of claim 1, wherein the means for removably attaching the substrate to an outer surface of a body comprises an adhesive.

12. The system of claim 1, wherein the means for removably attaching the substrate to an outer surface of a body comprises a band.

13. A method for determining a position and a change in the position of an anatomical structure using a surgical navigation system, the method comprising the steps of:

providing a surgical navigation system;

attaching a substrate in a removable manner to an outer surface of a body, the substrate having an associated sensor and having a positional device for determining a position of the anatomical structure relative to the sensor, wherein the positional device includes a fiber optic device attached to the substrate, the fiber optic device comprising a fiber and a means for attachment to the anatomical structure, and wherein the body includes an anatomical structure spaced interiorly from the outer surface;

determining a position of the anatomical structure relative to the sensor using the fiber optic device;

tracking the sensor with the surgical navigation system to determine a position of the sensor;

determining the global position of the anatomical structure by concatenating the position of the sensor and the position of the anatomical structure relative to the sensor;

tracking the position of the anatomical structure with the surgical navigation system; and displaying the position of the anatomical structure on a display unit.

14. The method of claim 13, wherein the fiber includes a serrated portion for the emission of light along a length of the fiber.

15. The method of claim 14, wherein the serrated portion is covered by a light absorbent material.

16. The method of claim 13, wherein the means for attachment comprises a pin and the fiber is attached to the pin, further comprising the step of removably attaching the pin to the anatomical structure.

17. The method of claim 13, further comprising the step of transcutaneously placing the means for attachment next to the anatomical structure through a sleeve with an impaction device.

18. The method of claim 13, wherein multiple positional devices simultaneously determine the position of the anatomical structure, and wherein the method further comprises the step of calibrating the multiple positional devices by using a calibration object to determine relative distances between the positional devices.

\* \* \* \* \*